(12) United States Patent
Tao

(10) Patent No.: US 11,101,033 B2
(45) Date of Patent: Aug. 24, 2021

(54) MEDICAL IMAGE AIDED DIAGNOSIS METHOD AND SYSTEM COMBINING IMAGE RECOGNITION AND REPORT EDITING

(71) Applicant: Peng Tao, Beijing (CN)

(72) Inventor: Peng Tao, Beijing (CN)

(73) Assignee: BEIJING SIGMA LIEDUN INFORMATION TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 16/833,512

(22) Filed: Mar. 28, 2020

(65) Prior Publication Data

US 2020/0303062 A1   Sep. 24, 2020

Related U.S. Application Data

(63) Continuation of application No. PCT/CN2018/108311, filed on Sep. 28, 2018.

(30) Foreign Application Priority Data

Sep. 28, 2017   (CN) .......................... 201710895420.4

(51) Int. Cl.
*G06K 9/00* (2006.01)
*G16H 30/40* (2018.01)
(Continued)

(52) U.S. Cl.
CPC .......... *G16H 30/40* (2018.01); *G06T 7/0014* (2013.01); *G06T 7/11* (2017.01); *G16H 30/20* (2018.01); *G06T 2207/30096* (2013.01)

(58) Field of Classification Search
CPC .......... G16H 30/40; G16H 30/20; G06T 7/11; G06T 7/0014; G06T 2207/30096
See application file for complete search history.

(56) References Cited

U.S. PATENT DOCUMENTS

| | | | |
|---|---|---|---|
| 2011/0137132 A1* | 6/2011 | Gustafson | A61B 5/7264 600/300 |
| 2012/0014559 A1* | 1/2012 | Suehling | G16H 30/40 382/103 |

(Continued)

*Primary Examiner* — Xin Jia
(74) *Attorney, Agent, or Firm* — Guosheng Wang; United States Research and Patent Firm

(57) ABSTRACT

A medical image aided diagnosis method and system combining image recognition and report editing. The medical image aided diagnosis method comprises the following steps S1, establishing an image semantic expression knowledge graph of medical images, S2, obtaining a medical image of a patient, determining a region of interest on a two-dimensional image, and providing a candidate focus option of the patient according to the image semantic expression knowledge graph and the region of interest; and S3, determining a focus type according to the region of interest and the candidate focus option; performing division to obtain a lesion region according to the focus type, and generating a structured report related to a region-of-interest of the medical image of the patient, and adding the lesion region and corresponding expression content of image semantics into a corresponding focus image library. In the method, medical image recognition is performed by combining an image semantic expression knowledge graph and a variety of machine leaning, sample images can be deeply accumulated, the image semantic expression knowledge graph can be continuously improved, and aided diagnosis capabilities of medical images can be enhanced.

10 Claims, 7 Drawing Sheets

(51) Int. Cl.
*G06T 7/11* (2017.01)
*G16H 30/20* (2018.01)
*G06T 7/00* (2017.01)

(56) References Cited

U.S. PATENT DOCUMENTS

| | | | |
|---|---|---|---|
| 2014/0219500 A1* | 8/2014 | Moehrle | G16H 15/00 382/103 |
| 2015/0265251 A1* | 9/2015 | Cho | A61B 8/085 600/437 |
| 2018/0276813 A1* | 9/2018 | Gur | G06T 7/11 |

* cited by examiner

MEDICAL IMAGE AIDED DIAGNOSIS METHOD AND SYSTEM COMBINING IMAGE RECOGNITION AND REPORT EDITING

TECHNICAL FIELD

The invention relates to a medical image aided diagnosis method, more particularly, to a medical image aided diagnosis method combining image recognition and report editing, and also to a corresponding medical image aided diagnosis system, which belong to the technical field of medical image aided diagnosis.

RELATED ART

It is well known that although general doctors in an image department have undergone a lot of learning in the classroom, they still have to continue to accept the advices of senior experts in internships and subsequent clinical practice of resident doctors. The advices are all in the specific diagnosis and treatment practice. The senior experts need to combine specific medical images to modify and correct image reports of the general doctors.

However, the current diagnosis for medical images has the following, problems.

1) Various organs and focuses displayed in medical images are highly isolated from corresponding descriptions in image reports, and the correlation is completely without system-level support. The correspondence and correlation between two parts of content depend entirely on the eyes and professional knowledge of readers and reviewers. As a result, when senior doctors review reports of junior doctors and when previous reports need to be reviewed during consultations and referrals, it is difficult to find corresponding image performance from focus descriptions in the reports, which is time-consuming and inefficient.

2) A structured report promoted by the Medical Image Association has the advantages of accurate focus descriptions and uniform description specifications, but it is cumbersome and inefficient in practice, which makes it difficult to apply and promote.

3) Existing deep learning methods applied in the field of medical images require a large amount of focus labeling, and a large number of labeled samples are not fully utilized and lack interpretability. In addition, the labeling of a traditional picture archiving and communication system (PACS) and the labeling in medical images require extra labor, and cannot be organically integrated with the existing daily work of image department doctors.

In order to solve the foregoing problems, many institutions have conducted a lot of research and exploration. However, the existing technical solutions do not effectively solve the problems in the prior art that a large number of labeled samples are not fully utilized and cannot be organically combined with the daily work of image department doctors. The expansibility of a generation system is not strong, so the accuracy of a dynamic diagnosis report cannot be improved in time. On the other hand, structured reporting in the field of images is an inevitable development direction in the field of medical image management. Without professional and structured reports, the concept of big data is false, data mining and online decision support cannot be achieved, the diagnosis cannot be graded based on the "golden criteria of diagnosis", and it is even less likely to provide treatment plan-oriented practical reports for clinical departments.

SUMMARY

In view of the deficiencies of the prior art, the primary technical problem to be solved by the invention is to provide a medical image aided diagnosis method combining image recognition and report editing.

Another technical problem to be solved by the invention is to provide a medical image aided diagnosis system combining image recognition and report editing.

In order to achieve the foregoing purpose of the invention, the invention adopts the following technical solutions.

According to a first aspect of embodiments of the invention, a medical image aided diagnosis method combining image recognition and report editing is provided. The method includes the following steps:

S1, establishing an image semantic representation knowledge graph of medical images;

S2, obtaining a medical image of a patient, determining a region of interest (ROI) on a two-dimensional image, and providing candidate focus options of the patient according to the image semantic representation knowledge graph and the ROI; and S3, determining a focus type according to the ROI and the candidate focus options, performing division (extraction) to obtain a lesion region according to the focus type, generating a structured report related to the ROI of the medical image of the patient, and adding the lesion region and corresponding image semantic representation into a corresponding focus image library.

Preferably, step S1 further includes the following steps:

S11, forming a basic list of named entities based on a standardized dictionary library in the field of medical images;

S12, forming a characteristic description text specification for named entities by analyzing historically accumulated medical image reports in the focus image library; and S13, transforming the obtained characteristic description text specification for named entities into image semantic representation based on expert knowledge and a local lesion image corresponding to a specific focus type, and jointly establishing the image semantic representation knowledge graph by each named entity, and an image and image semantic representation corresponding to the named entity.

Preferably, step S3 further includes the following steps:

S301, performing localization analysis on the ROI based on a focus type to which the ROI belongs, calculating a spatial position of the ROI, and performing division (extraction) to obtain a lesion region.

Preferably, step S3 further includes the following steps:

S311, performing localization analysis on the determined ROI based on a focus type to which the ROI belongs, determining the focus type to which the ROI belongs, extending the determined ROI from a two-dimensional image to a three-dimensional stereoscopic image or a two-dimensional dynamic image, and performing division (extraction) to obtain a lesion region from a whole image.

Preferably, when an image type is a three-dimensional image, step S311 further includes the following steps:

step 1: calling a gray value of the two-dimensional image based on a focus type determined by an expert in combination with shape and texture features corresponding to the focus type, dividing the lesion region according to a connection relationship of organs, and obtaining a main closed region of a closed core focus region corresponding to the lesion region in a two-dimensional image section;

step 2: extending to previous and next images in a spatial sequence of the two-dimensional image based on the main closed region, dividing the lesion region according to the connection relationship of organs based on shape and texture features corresponding to the focus type, and obtaining a closed region that matches the description of the focus type;

step 3: continuing the operation in step 2, performing a mathematical morphological closed operation in a three-dimensional space, removing other regions connected to the closed core focus region in the three-dimensional space until the closed core focus region no longer grows, and delineating a closed core focus region edge; and step 4: calculating maximum and minimum values of X, Y, and Z axes in edge pixel point coordinates of the closed core focus region, so as to form a three-dimensional cube region.

Preferably, when an image type is a two-dimensional dynamic image, step S311 further includes the following steps:

step 1: pre-processing each frame in a dynamic image, and outputting a relatively fixed image of a human organ region;

step 2: obtaining a complete sequence of observation frames with relatively fixed probe positions in the dynamic image; and step 3: completely obtaining a complete sequence of observation frames corresponding to the ROI based on the ROI, the determined focus type, and a sequence of observation frames in which the ROI is determined.

Preferably, when a scanning probe has a position movement sensor, obtaining a complete sequence of observation frames with relatively fixed probe positions in the dynamic image in step 2 includes the following steps:

determining, based on the position movement sensor, whether the probe is moving fast;

if the probe is moving fast, considering that a detection instrument is looking for the ROI, otherwise, considering that the probe is basically stationary and is focusing on the change of an image in a certain region with time; and determining a complete sequence of observation frames with relatively fixed probe positions based on the change of position with time.

Preferably, when a scanning probe does not have a position movement sensor, obtaining a complete sequence of observation frames with relatively fixed probe positions in the dynamic image in step 2 includes the following steps:

analyzing the dynamic image in real time to determine whether the probe is moving fast, if the probe is moving fast, considering to be looking for the ROI, otherwise, considering that the probe is basically stationary and is focusing on the change of an image in a certain region with time; and determining a complete sequence of observation frames of the same scene based on the analysis of adjacent frames and similar scenes.

Preferably, the structured report contains a hyperlink of image semantic representation corresponding to a determined lesion region related to the lesion region, and the lesion region displayed in the image and the image semantic representation corresponding to the lesion region can be viewed simultaneously by clicking the hyperlink.

Preferably, when the candidate focus options do not match the ROI, the image semantic representation corresponding to the ROI is input and sent to other experts for verification, and after the verification is passed, the lesion region and the corresponding image semantic representation are added to the corresponding focus image library.

According to a second aspect of the embodiments of the invention, a medical image aided diagnosis system combining image recognition and report editing is provided. The system includes: a knowledge graph establishment module, an information acquisition module, an ROI determination module, a candidate focus option generation module, a lesion region determination module, a report generation module, and a correction module.

The knowledge graph establishment module is configured to establish an image semantic representation knowledge graph according to a standardized dictionary library in the field of images and historically accumulated medical image report analysis.

The information acquisition module is configured to acquire a medical image of a patient.

The ROI determination module is configured to determine an ROI of the medical image of the patient.

The candidate focus option generation module is configured to provide candidate focus options of the patient according to the image semantic representation knowledge graph and the ROI.

The lesion region determination module is configured to determine a focus type according to the ROI and the candidate focus options, and perform division (extraction) to obtain a lesion region according to the focus type.

The report generation module is configured to generate a structured report related to the ROI of the medical image of the patient according to the divided lesion region and corresponding image semantic representation.

The correction module is configured to add the lesion region and the corresponding image semantic representation into a corresponding focus image library.

Preferably, the lesion region determination module includes a focus type determination unit and a lesion region determination unit.

The focus type determination unit is configured to determine a focus type in the provided candidate focus options according to the ROI.

The lesion region determination unit is configured to perform localization analysis on the ROI, perform division to obtain a lesion region, and determine a lesion type corresponding to the lesion region according to the image semantic representation knowledge graph.

The lesion region determination module is configured to perform localization analysis on the ROI, calculate a spatial position of the ROI, and perform division to obtain a lesion region.

According to the medical image aided diagnosis method combining image recognition and report editing provided by the invention, an image semantic representation knowledge graph and a variety of machine learning are combined to perform medical image recognition, sample images can be systematically and deeply accumulated, and the image semantic representation knowledge graph can be continuously improved, so that labeled focuses of many images can be continuously collected under the same sub-label. In addition, as more and more labeled focuses are accumulated, labeling of the focuses can be continuously refined by means of machine learning in combination with manual in-depth research, thereby further enriching the measures of radiomics and enhancing aided analysis capabilities of medical images.

BRIEF DESCRIPTION OF THE DRAWINGS

FIG. 10b is a schematic diagram of labeling a pulmonary air part after threshold processing and connectivity analysis of the schematic structure diagram shown in FIG. 10a.

DETAILED DESCRIPTION

The present invention is described in detail below with reference to the accompanying drawings and specific embodiments.

According to a medical image aided diagnosis method combining image recognition and report editing provided by the invention, based on preliminary medical anatomical structure expressions in medical images and preliminary focus (focus region) recognition capabilities, the current process of producing, editing and reviewing image reports by doctors is changed. By sketching out or pointing to a certain physiological structure (organ, tissue or focus) that belongs to a specific image region (no matter the region is a portion of a two-dimensional splice in a two-dimensional image or a three-dimensional image, or a portion of a specific screenshot in a dynamic image), an image report description content entry (i.e. a content of an image semantic representation) corresponding to the physiological structure can be generated automatically or semi-automatically, and named entities in the entry are linked to a specific region of a corresponding image.

Compared with the prior art, the invention is a medical image reading machine learning method and system simulating interactive training. By reconstructing a reading report process commonly used by image department doctors, the efficiency of reading and report generation, as well as the efficiency of report editing and reviewing, can be greatly improved Meanwhile, an artificial intelligent reading technical system capable of continuing to communicate with superior doctors and continuously learning to improve reading and reporting capabilities is constructed.

Figure 1:
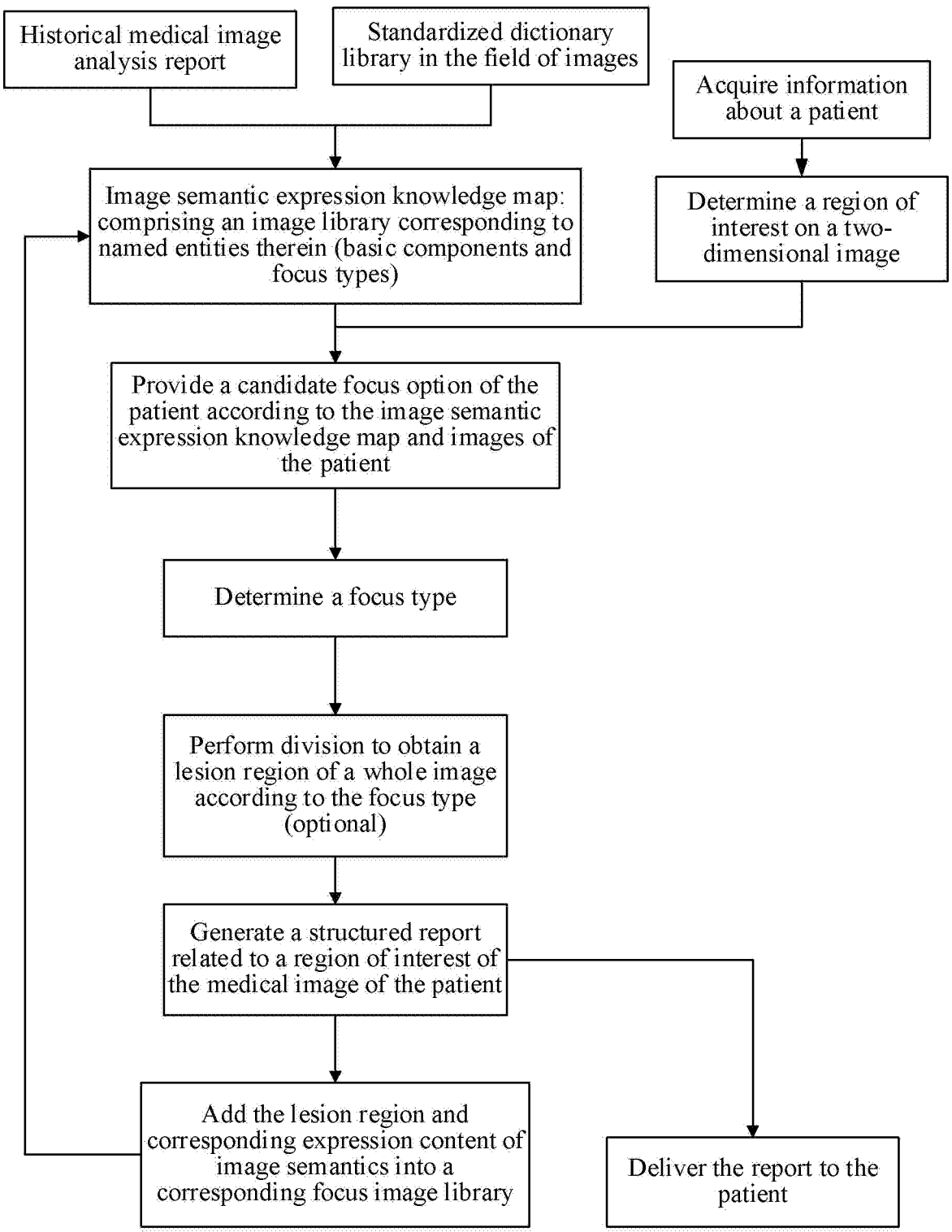
FIG. 1 is a flowchart of a medical image aided diagnosis method combining image recognition and report editing according to the invention.

As shown in FIG. 1, the medical image aided diagnosis method combining image recognition and report editing provided by the invention mainly includes the following steps. Firstly, an image semantic representation knowledge graph is established according to a standardized dictionary library in the field of images and analysis of historically accumulated medical image reports in a focus image library. Subsequently, a medical image of a patient is acquired to determine an ROI on the two-dimensional image of the patient, and then candidate focus options of the patient are provided according to the image semantic representation knowledge graph and the ROI. Finally, a focus type is determined according to the ROI and the candidate focus options, a lesion region is obtained through division according to the focus type, a structured report related to the ROI of the medical image of the patient is generated. Meanwhile, the lesion region and corresponding image semantic representation contents are added into the corresponding focus image library, and the structured report is delivered to the patient. The process will be described in detail below.

In S1, an image semantic representation knowledge graph is established according to a standardized dictionary library in the field of images and accumulated medical image report analysis in a focus image library. The image semantic representation knowledge graph here is a general term of a medical image report knowledge graph and an image semantic system.

The establishment of an image semantic representation knowledge graph for the description of various organs, various focuses and their lesions, according to the standardized dictionary library in the field of images and the accumulated medical image report analysis, specifically includes the following steps.

In S11, a basic list of named entities is formed based on the standardized dictionary library in the field of images.

The basic list of named entities is formed based on a standardized dictionary library in the field of images (in the embodiments provided by the invention, based on the standardized dictionary library RADELX). The named entities include various organs and focuses.

In S12, a characteristic description text specification for each named entity is formed by analyzing the accumulated medical image reports in the focus image library.

Through the analysis and expert knowledge of massive medical image reports about different types of medical images (including, but not limited to, lung CT, molybdenum target, cerebrovascular MRI, cardiovascular ultrasound, and the like), various types of characteristic description text specifications corresponding to various organ lesions and focuses are formed.

The medical image reports contain state descriptions of various organs and some local focus descriptions therein. A current trend is to establish an image reporting and data system (RADS) structured report covering the Radiological Society of North America (RSNA) and the American College of Radiology (ACR) based on a standardized dictionary library RADELX in the field of images. The structured report will clearly describe the position, nature and grade of a lesion in an image. In general, a spatial position relationship between the focuses of specific types and the organs is relatively clear, and there are relatively specific gray distributions (including, the distribution of gray in spatial positions) and texture structures, so there is a clear semantic representation to the image.

In S13, the characteristic description text specification for each named entity obtained is transformed into the image semantics representation based on the expert knowledge, and then the image semantic representation knowledge graph of the medical image is created by each named entity, in cooperation with the image and the image semantics representation corresponding to the named entity.

Based on the expert knowledge, the characteristic description text specification for the named entities is transformed into the image semantics representation, which includes spatial attributes, gray distributions and texture structure descriptions, thereby forming the image semantic representation knowledge graph in a medical ontology involved in an image report. The image semantic representation knowledge graph, in addition to structured descriptions of text and data, includes labeled samples of images (most of them being local images) corresponding to each named entity (including easy-to-recognize basic components and focuses) type.

Figure 2:
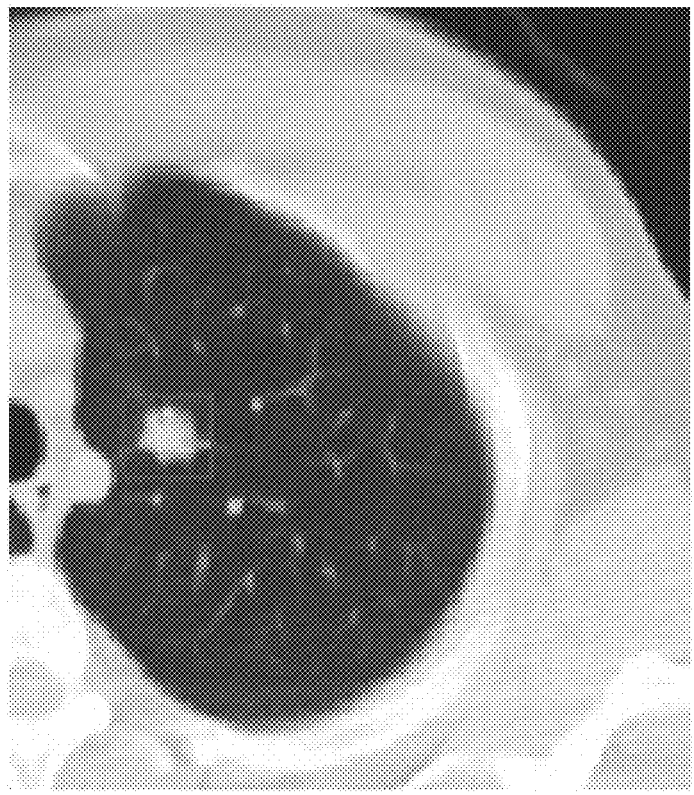
FIG. 2 is a schematic image diagram of solid nodules in an embodiment provided by the invention.

The following describes the structure and content of the image semantic representation knowledge graph with several specific embodiments. For example:

1. An image graph of a solid nodule is shown in FIG. 2, and its corresponding image semantics representation is:

Position-included in: 1) left and right lungs; 2) tracheae and bronchi.

Position-neighbor: 1) surrounded by pulmonary air, or 2) connected to lung walls, or 3) connected to blood vessels, or 4) connected to bronchi.

Shape: nearly round (three-dimensional: spherical) or oval (three-dimensional: cobblestone shape).

Size classification:
Micro nodules: diameter of less than 5 mm;
Small nodules: diameter of 5-10 mm;
Nodules: diameter of 10-20 mm;
Mass: diameter of greater than 20 mm.
Density-spatial distribution:
Boundary: clear (sharply different gray distribution), with or without burrs.

Corresponding lesion:

The probability of malignant micro nodules is less than 1%, and the follow-up interval is confirmed from 6 to 12 months.

The probability of malignant small nodules is 25% to 30%, and the follow-up interval is 3 to 6 months for CT review (LDCT is recommended).

A lung nodule grows faster during follow-up, biopsy or surgery is recommended (based on growth rate).

Nodules and masses are more likely to be malignant, biopsy or surgery is to be performed.

2. A ground glass opacity (GGO) is also called a frosted glass nodule, and the corresponding image semantic representation is:

Position-included in: 1) left and right lungs; 2) tracheae and bronchi.

Position-neighbor: 1) surrounded by pulmonary air, 2) connected to lung walls, 3) connected to blood vessels, 4) connected to bronchi.

Figure 3:
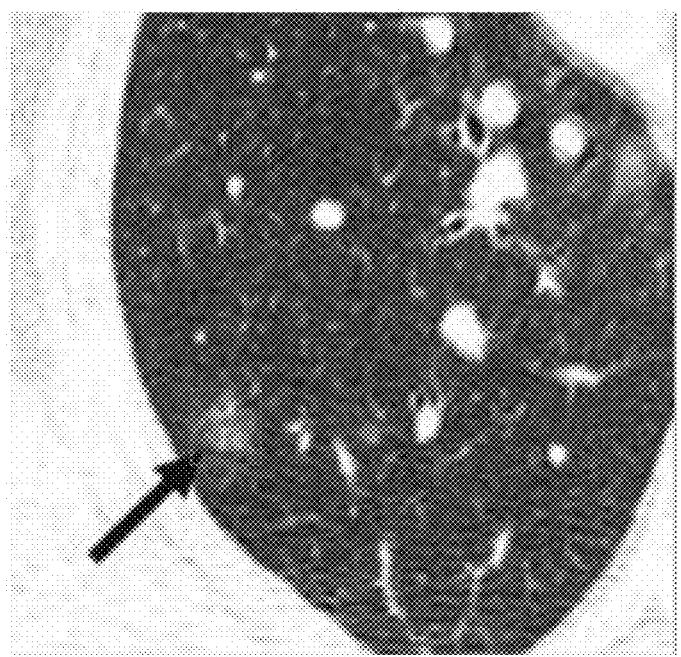
FIG. 3 is a schematic image diagram of pure ground glass opacity (PGGO) in an embodiment provided by the invention.
Figure 4:
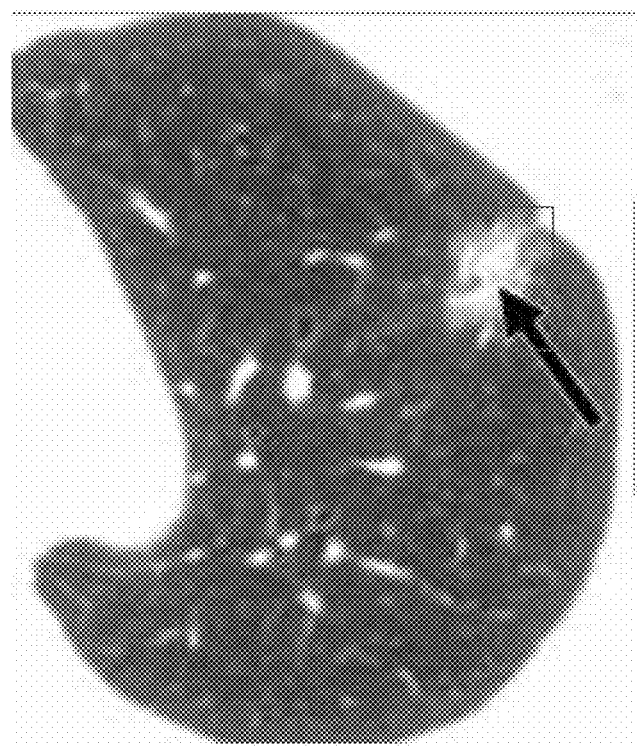
FIG. 4 is a schematic image diagram of mixed ground glass opacity (MGGO) in an embodiment provided by the invention.

Type: pure GGO (PGGO) and mixed GGO (MGGO) as shown in FIG. 3 and FIG. 4 respectively.

Density-spatial distribution: slightly high-density opacity (ground glass) on a low-density background of a lung field, or partial high-density opacity (solid components with density distribution similar to solid nodules). The PGGO has no solid components (excluding high-density opacity), and the MGGO contains high-density opacity part.

Shape: stacked in blocks.
Boundary: clear or unclear, with many burrs.

3. Cavity has a corresponding image semantic representation as follows:

Position-included in: 1) left and right lungs.
Density-spatial distribution:
Wormy appearance: wall-less cavity, low-density opacity part surrounded by slightly high-density opacity;
Thin-walled: low-density image part surrounded by thin-wall (high-density opacity);

Thick-walled: low-density image part surrounded by thick-wall (high-density opacity).

Figure 5:
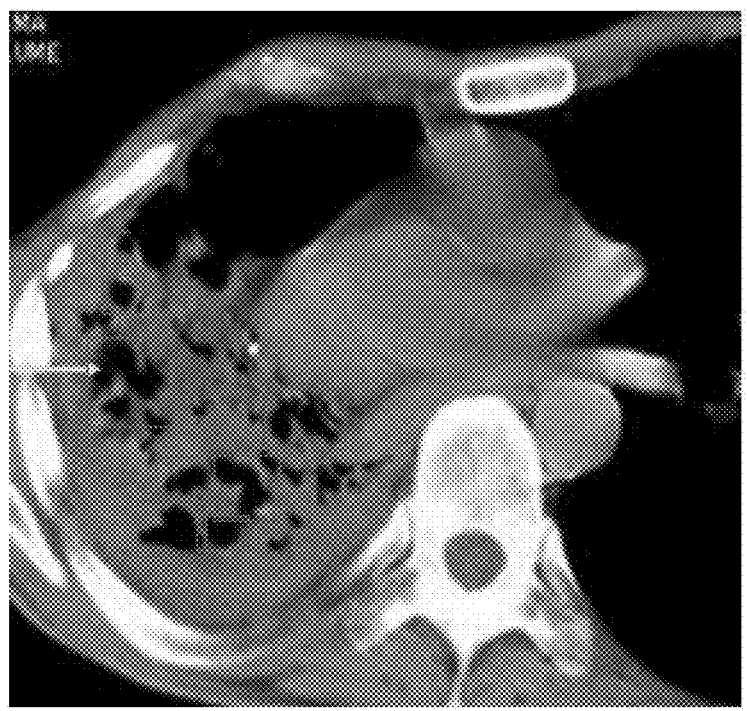
FIG. 5 is a schematic image diagram of a wall-less cavity in an embodiment provided by the invention.
Figure 6:
FIG. 6 is a schematic image diagram of a thin-walled cavity in an embodiment provided by the invention.
Figure 7:
FIG. 7 is a schematic image diagram of a thick-walled cavity in an embodiment provided by the invention.

Corresponding lesion:
Wormy appearance cavity: caseous lobar pneumonia and the like, as shown in FIG. 5;
Thin-walled cavity: secondary pulmonary tuberculosis and the like, as shown in FIG. 6;
Thick-walled cavity: tuberculoma, lung squamous cell carcinoma and the like, as shown in FIG. 7.

After initialization, the medical image aided diagnosis system has preliminarily constructed an image semantic representation knowledge graph, forms different attribute descriptions for corresponding organs, lesions and focuses shown in medical images that are scanned in different types, different purposes and different parts. The attribute descriptions (qualitative or quantitative) may be calculated. That is, through calculation from the corresponding feature extraction after the recognition of a specific object in the medical image, the attribute descriptions are obtained such as a relative spatial position range of a specific focus, an average density value, a standard deviation, entropy, roundness or sphericity, edge burr, edge sharpness, a histogram, a density distribution map of a distance around the center, and a correlation matrix of texture expression in the image.

In S2, a medical image of a patient is acquired, a system pre-processes, recognizes and positions some basic and easy-to-recognize components of the medical image of the patient, and then candidate focus options of the patient are provided, based on the basic information and an ROI on a two-dimensional image drawn by an expert, according to the image semantic representation knowledge graph and the ROI.

Figure 8:
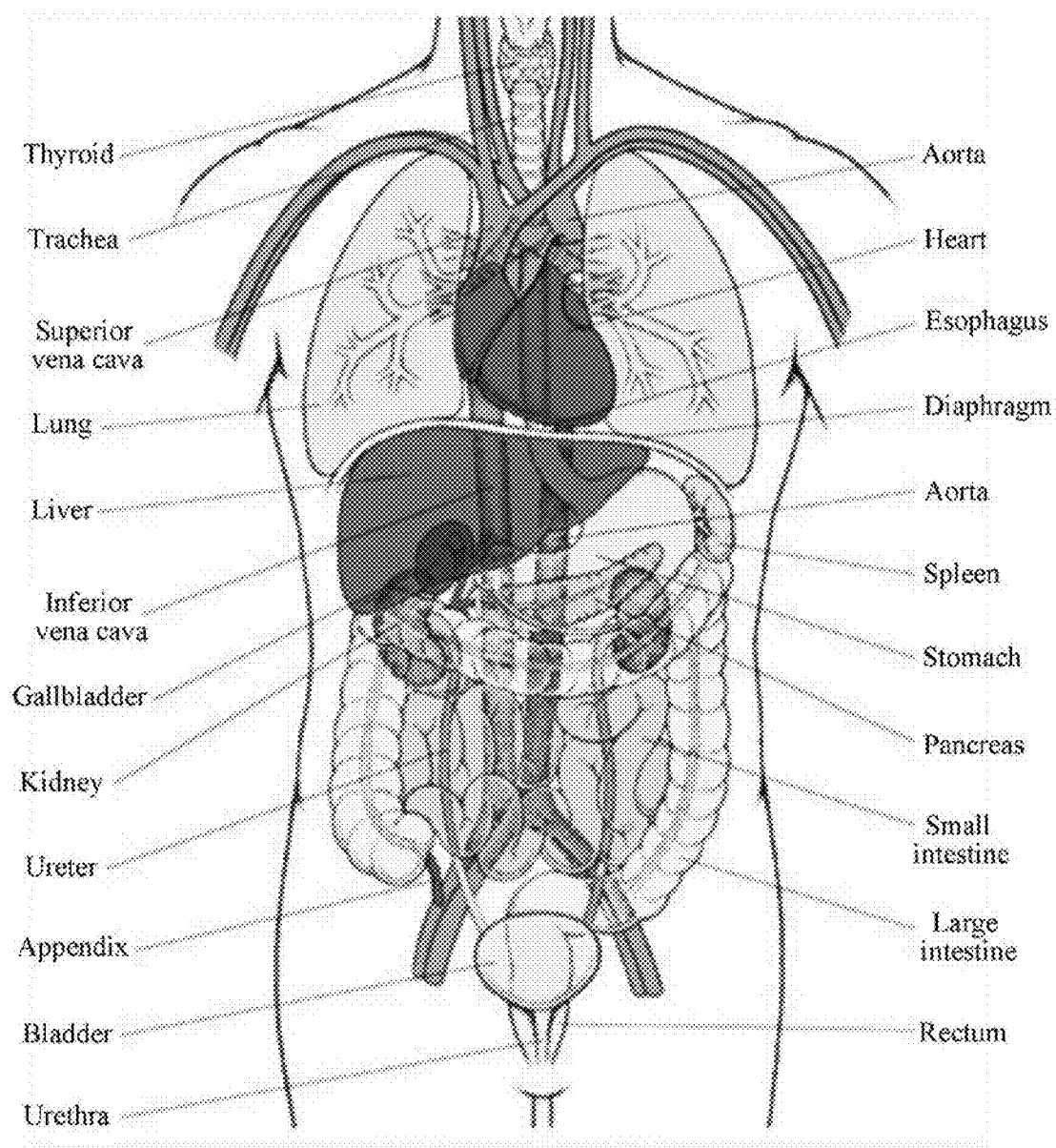
FIG. 8 is a distribution diagram of organs in the upper torso of a human body in an embodiment provided by the invention.
Figure 9:
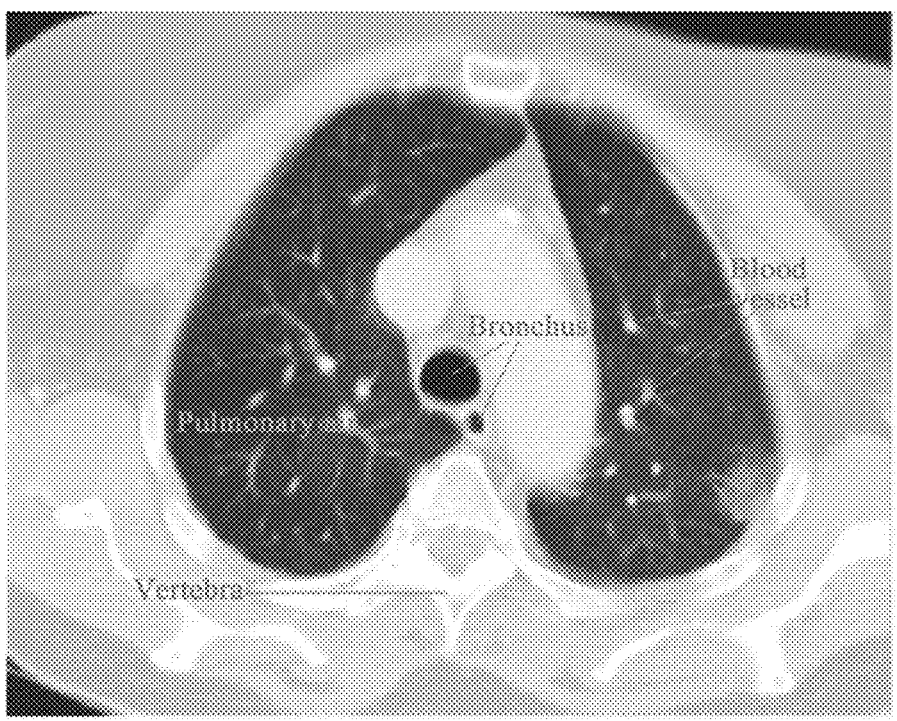
FIG. 9 is a schematic structure diagram of a specific two-dimensional section of human chest and lung CT and a corresponding series of easy-to-recognize organs in an embodiment provided by the invention.
Figure 10A:
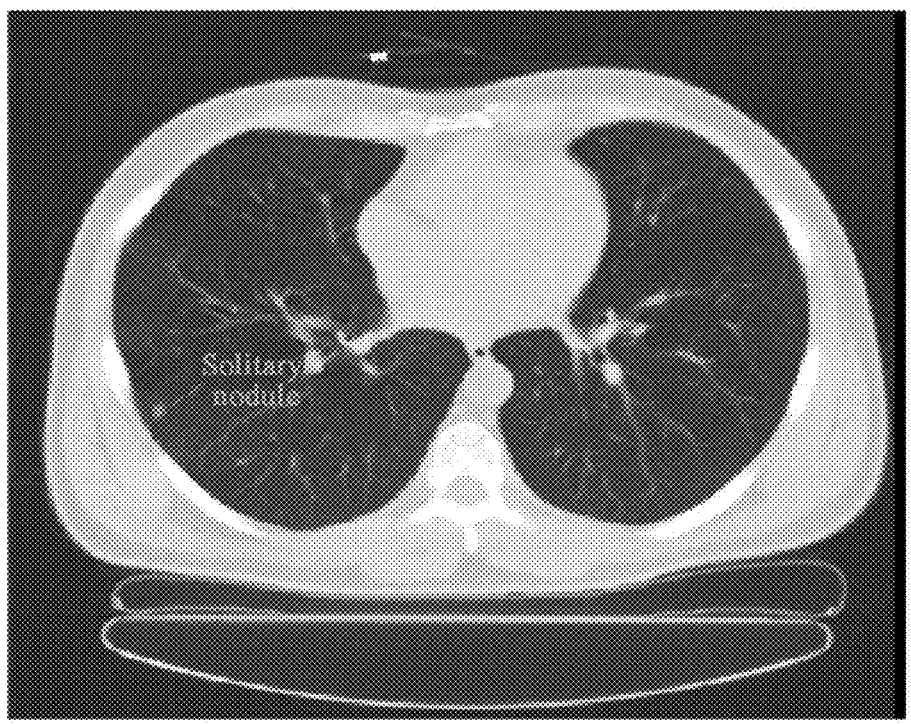
FIG. 10a is a schematic structure diagram of a specific two-dimensional section view of human chest and lung CT and corresponding labeling of a pulmonary air part in an embodiment provided by the invention.
Figure 10B:
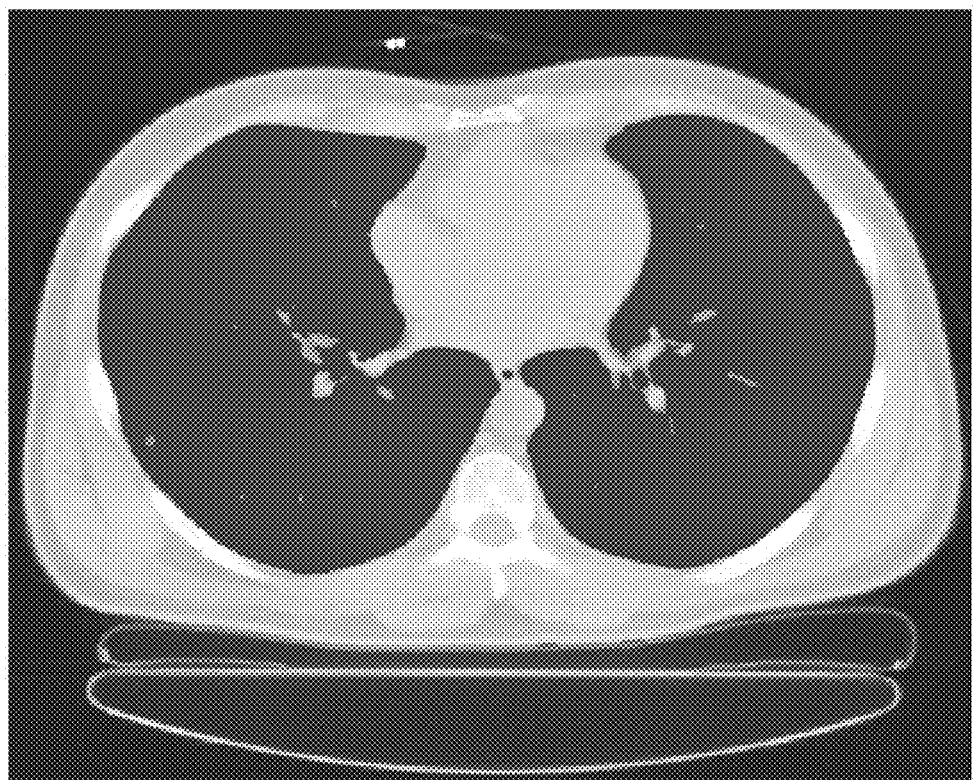

To generate a structured report, it is necessary to first acquire personal information of the patient and the medical image of the patient. In the invention, the technical means for obtaining the medical image of the patient include, but are not limited to, chest and lung CT, abdominal CT, cerebrovascular MRI, breast MRI, abdominal ultrasound, and the like. After obtaining the medical image of the patient, the system pre-processes, recognizes and positions some basic and easy-to-recognize components of the medical image of the patient. That is, it is necessary to first recognize some basic components such as pulmonary air, bones, and vertebrae. Then, by recognizing and positioning the basic components, in combination with a spatial position relationship between the ROI manually drawn by the expert and the recognized basic components, a list of possible focus options inside the ROI is preliminarily determined for further screening Human organs generally have relatively fixed positions. Their positions in the medical images and image display (gray value on the image, etc.) are generally more obvious, and are easy to recognize, localize (position), and deconstruct. FIG. 8 is a distribution diagram of organs in the upper torso of a human body. Lung CT (plain scan or enhanced) is taken as an example. It is easier to distinguish vertebrae, trachea, bronchi, lymph, pulmonary air, blood vessels and other parts, as well as some of the large variations, such as pleural and pulmonary effusion and large lesions. In MRI images and ultrasound dynamic images, it is also easy to recognize and accurately position the organ parts using human eyes or an image diagnosis system of a computer. The organ parts are relatively easy to use image recognition algorithms, threshold analysis, edge detection, and position information to carry out preliminary focus recognition and positioning FIG. 9 is a cross-sectional view of a three-dimensional CT chest and lung image. The high-brightness parts are bones, the bottom middle triangle (middle gray) parts are vertebrae, large connected regions of the black (HU low density) parts on internal left and right sides are pulmonary air, and black round areas in the center part are a cross-sectional view of bronchi Blood vessels are those brighter line segments or round oval cross sections surrounded by pulmonary air. FIG. 10b shows a pulmonary air part labeled (red part) after threshold processing and connectivity analysis of an original lung CT image (FIG. 10a is a two-dimensional screenshot). The recognition and localization of this pulmonary air part, aid and limit the present system to analyze and acquire a possible focus type when the experts draw an ROI in the pulmonary air part. Only the focus types for the region within or adjacent to the red part need to be further analyzed (texture analysis, density-spatial analysis and convolutional neural network matching, etc.). High-probability focus types are introduced by the system for experts to choose.

After obtaining the medical image of the patient, the expert determines an ROI on the two-dimensional image based on the medical image of the patient, that is, a region where a lesion may be considered to exist by the expert. For example, if an ROI body drawn by a radiologist in a lung CT examination image is in the lung and connected to blood vessels, and the region is surrounded by pulmonary air (the recognition and positioning of pulmonary air is shown in FIG. 10), the medical image aided diagnosis system may automatically analyze the position features. By division algorithms in the ROI and HU density distribution and texture analysis, it is estimated that this is highly probably a nodule connected to the blood vessels, it may be a frosted glass nodule if its solid degree is not high, or a lung infection if there are large areas of messy texture. Based on the characteristics, as well as the image semantic representation knowledge graph and the ROI sketched out by the expert, the medical image aided diagnosis system may automatically pop up a list of options after preliminary calculation. The list ranks a plurality of description options based on the possibility, that is, candidate focus options of the patient. There may be one or more candidate focus options.

Specifically, after an expert delineates the ROI, preliminary localization analysis is performed on the ROI. Based on the position, texture, gray distribution and other features on the two-dimensional image cross section of the ROI, according to an image feature model corresponding to the named entities (such as certain several focuses) in the image semantic representation knowledge graph, the type of the named entities (specific types of focuses), which may contain similar characteristics in the ROI labeled on the two-dimensional image cross section, is determined. Then, the type of the named entities is provided to the expert through an interactive interface (which may be an option form of graphical interfaces or a voice response form) for the expert to choose.

The determination of the ROI here may be completed by an expert manually clicking on a computer or through an image recognition algorithm. The expert manual completion is that a doctor browses and observes through a medical image display system such as PACS, and finds some suspected lesion regions. By manually delineating on the two-dimensional image cross section, the form of a closed curve is drawn, that is, an ROI is positioned on a two-dimensional cross section.

The completion through an image recognition algorithm is that a computer with a certain degree of reading (image reading) capability performs recognition positioning and automatic prompt through some types of focus recognition algorithms (for example, traditional image recognition algorithms based on features or rules; or deep learning algorithms such as CNN or RNN; assistance with transfer learning or reinforcement learning) Or, by comparing with normal medical image of the same type, a region where the medical image of the patient is different from the normal medical image is found and determined as the ROI.

In S3, the focus type is determined according to the ROI and the candidate focus options. The lesion region is obtained through division according to the focus type. The structured report related to the ROI of the medical image of the patient is generated, and the lesion region and the corresponding image semantics representation are added into the corresponding focus image library.

In S301, localization is performed on the ROI based on the determined focus type to which the ROI belongs, to calculate the spatial position of the ROI and acquire the lesion region.

The focus options are determined according to the ROI delineated by the expert and the candidate focus options to further determine the focus type. Localization analysis is performed on the ROI, a spatial position of the ROI is calculated, a lesion region is obtained through division, a structured report related to the ROI of the medical image of the patient is generated, and the lesion region and corresponding image semantic representation are added into a corresponding focus image library. After the ROI is determined, localization analysis is performed on the ROI based on the determined focus type to which the ROI belongs, a spatial position of the ROI is calculated, and a lesion region is obtained through division. The operation specifically includes the following steps.

In S3011, the focus type to which the ROI belongs is determined according to the ROI and the candidate focus options.

As mentioned above, human organs generally have relatively fixed positions. The positions in medical images and image display (gray value on the image, etc.) are generally more obvious, and are easy to recognize, position, and deconstruct. For the medical image of the patient, localization analysis is performed on the delineated ROI, and a focus type to which the ROI belongs is determined according to the delineated ROI and the selected focus option.

In S3012, a spatial position of the ROI is calculated based on the determined focus type of the ROI, and a lesion region is obtained through division.

Each type of organ has its unique spatial position, gray spatial distribution, and texture attributes. For example, solitary small pulmonary nodules are surrounded by pulmonary air in isolation. After a three-dimensional image shows threshold processing and connected branch analysis, the surroundings are all air branch (HU density is below a certain threshold and in the lung) surroundings. The distribution of HU density values inside the nodule branch with the branch center conforms to a certain distribution. The small pulmonary nodules connected to the blood vessels are basically surrounded by pulmonary air, but may be connected to tracheae/bronchi, pleurae, and lung lobes through one or more blood vessels (high density). After a three-dimensional image shows threshold processing and connected branch analysis, the surroundings are all air branch (HU density is below a certain threshold and in the lung) surroundings, but there are high-density narrow-channel blood vessel branches (HU density higher than a certain threshold and in the lung) connected. The high-density narrow-channel blood vessel branches may be filtered in the image through an Opening operator of Morphological Analysis (spherical structural elements at different scales).

The internal HU density-spatial distribution is somewhat different from that of the solitary nodules. A surrounding part of the small pulmonary nodules connected to a lung wall is surrounded by pulmonary air, but one of its side is close to the lung wall. In the three-dimensional image, by means of threshold processing and connected branch analysis, it may be filtered in the image through an Opening operator of Morphological Analysis (spherical structural elements at different scales), and a focus may be obtained through division. There are other types of nodules such as frosted glass nodules.

The spatial position and surrounding region of the region are calculated based on the focus type determined by the medical image of the patient, that is, it is determined whether the ROI is adjacent to certain organs in a certain part or organ, and multiple methods (for example, threshold calculation, edge extraction and texture analysis) may be used in the ROI for division to further obtain possible focus or lesion regions therein through division. To obtain the lesion region in the ROI by division, the gray value of the two-dimensional image may be used, and based on the threshold or texture features of the focus type, a region that does not meet the threshold or texture feature requirements is divided as the lesion region. That is, by calculating the matching degree between the ROI and the known focus type, a possible focus or lesion region is obtained.

The structured report is generated by the obtained lesion region through division and the image semantics representation corresponding to the lesion region, together with patient information. The image semantic representation corresponding to the lesion region is a structured lesion description entry, which will generate determined focus options and attributes thereof (including the size, burr, clarity, average density value and HU histogram distribution of the focus) to be related to the ROI (or determined as a focus region) of the medical image. In the embodiments provided by the invention, the named entity part of the focus option determined in the structured report is a hyperlink related to the ROI. Specifically, the hyperlink is a hyperlink of the image semantic representation corresponding to the determined lesion region related to the lesion region. The lesion region and the image semantic representation corresponding to the lesion region (an ROI of a two-dimensional image, or a space-time segment from a three-dimensional image and a two-dimensional dynamic image) may be viewed simultaneously by clicking the hyperlink. The tediousness of finding a corresponding image in an image library according to image semantic representation corresponding to a lesion region in the existing report is effectively solved, and the efficiency of viewing the report is improved.

After generating the structured report, the lesion region and the corresponding image semantic representation are added into the corresponding lesion image library, as a sample accumulation for subsequent update and supplement of the image semantic representation knowledge graph, so that experts can complete accumulation of samples in the working process without extra human and financial resources to specifically conduct data mining, thereby improving the use efficiency of the structured report.

In the invention, an image semantic representation knowledge graph and a variety of machine learning, especially deep learning and reinforcement learning, are combined to perform medical image recognition. One advantage is that sample images can be systematically and deeply accumulated, and labeled focuses of many images can be continuously collected under the same sub-label. The so-called evolution is, on the one hand, a quantity accumulation. As more and more sample images of focuses with the same label are accumulated, the number of samples available for deep learning needs to continue to increase. Therefore, regardless of the use of algorithms such as CNN, RNN, DNN, or LSTM, the increase of samples generally leads to the enhancement of recognition capabilities and the improvement of recognition sensitivity and specificity. This is obvious. On the other hand, as more and more labeled focuses are accumulated, labeling of the focuses can be continuously refined by means of machine learning in combination with manual in-depth research, thereby further enriching the measures of radiomics to continuously refine image performance types of focuses. That is to say, for the original disease attribute description, types will be further increased, or quantitative description points will be further increased. For the former, if it is possible to find MGGO and nodules with different spatial-density distributions, new subtypes are added. For the latter, such as an edge of a focus, new measures may be added, such as edge burr. The increase in parameters may enhance the accuracy of predicting the degree of malignancy of the focus based on CT or MRI images.

Further, in combination with the focus type description of the image semantic representation knowledge graph, referring to a well-recognized obtained focus recognition model, the medical image aided diagnosis system will easily adopt transfer learning and other means to quickly learn some new or fewer samples of focuses. For example, breast MM masses and non-tumor-like enhanced focuses have many similarities of spatial-density distribution to lung CT nodules and GGO focuses, but they are different in specific parameters. The characteristics are very suitable for cross-domain transfer learning (a parameter model obtained by using, other focus samples with certain image performance similarity is applied to the focus sample for parameter adjustment), or Borrowed Strength parameter estimation when there are not sufficient focus samples with a certain type or label.

Second Embodiment

The second embodiment of the invention provides a medical image aided diagnosis method combining image recognition and report editing. The difference from the first embodiment is as follows:

First, in step S3 of the first embodiment, after the medical image of the patient is acquired, the determined ROI is extended from a two-dimensional image to a three-dimensional stereoscopic image or a two-dimensional dynamic image (video-like images that change with time), localization analysis is performed on the ROI based on the focus types included in the ROI, a spatial, position of the ROI is calculated, and the lesion region is obtained through division from the whole image.

Specifically, after the ROI is determined, performing localization analysis on the ROI and performing division to obtain a lesion region from the whole image in the following steps.

Localization analysis is performed on the determined ROI, and a focus type to which the ROI belongs is determined.

The determined ROI is extended from a two-dimensional image to a three-dimensional stereoscopic image or a two-dimensional dynamic image, and a lesion region of a whole image is obtained through division.

Generally speaking, considering the convenience of operation, users preliminarily delineate on the two-dimensional image cross section. A corresponding rectangular region or cubic region (obtained by CT, MRI, and the like) or a dynamic image (obtained by ultrasound) is further formed from the ROI delineated on the two-dimensional medical image of the patient. By calculating the matching degree between the ROI and known focus types, possible focus or lesion regions are obtained.

Then, localization analysis is performed to determine the focus type of the ROI.

The labeling, delineating and localization of the certain ROI or focus in the three-dimensional image obtained based on CT or MRI is generally limited to a two-dimensional image of a spatial cross section. The ROI of the cross section is delineated and further expanded to neighboring multiple two-dimensional frames adjacent in a front-back direction (in an up or down direction) based on similar texture gray distribution. The steps are as follows:

In step 1, based on a focus type determined by an expert, and shape and texture features corresponding to the focus type, a gray value of a two-dimensional image is used to delineate based on threshold or texture features of the focus type. In some cases, a mathematical morphology operator or other operators for the two-dimensional image are further used to divide certain focuses (for example, solid nodules connected to a lung wall, or masses connected to glands, each group is similar in pixel gray and texture features) from the organs to which the focuses connects, so as to obtain a main closed region of one or more closed core focus regions corresponding to the focus (that is, a lesion region) in a two-dimensional sub-image (frame) cross section.

The closed core focus region needs to meet the following two points.

(1) The closed core focus region is completely contained in the delineated ROI (will not be connected to the outside).

(2) The proportion of pixels of the closed core focus region to the pixels of the ROI should not be lower than a certain number (such as 30%).

In step 2, based on the main closed region of the image, previous and next images in a spatial sequence of the image is divided according to the threshold or texture features of the focus type. In some cases, a mathematical morphology operator or other division operators of the two-dimensional image are further used to divide certain focuses connected to a certain part of an organ to obtain one or more closed regions that match the description of the focus type. In the regions, only closed regions that are three-dimensionally connected to the previously identified main closed regions (generally treated as 6-neighborhood connections) are merged into the closed core focus regions.

In step 3, the operation in step 2 is continued, and a mathematical morphological closed operation in a three-dimensional space is performed to filter out other regions (in terms of masses and nodules, they are some catheters, blood vessels and organ glands) connected to the closed core focus region in the three-dimensional space until the closed core focus region no longer expands.

In step 4, a closed core focus region edge is thus delineated, and labeled at the pixel level. Meanwhile, maximum and minimum values of X, Y, and Z axes in edge pixel point coordinates of the closed core focus region are calculated, so as to form a space cube. That is, the three-dimensional cube region include the lesion region.

For a dynamic image based on ultrasound (B-mode ultrasound), the user can label and localize the ROI or the focus, which is generally limited to a static image at a specific time segment (in ultrasound, it is often one or a few frames in image frames which are scanned in a time segment at a fixed point) A complete delineation of the ROI or focus, is to further extend the delineation of the ROI in a cross section by the user to adjacent two-dimensional frames of the dynamic image through an algorithm (spatial neighboring, texture, gray and the like) by a computer.

The characteristic of B-mode ultrasound is that doctors are constantly moving probes of detection instruments, and part of images of parts monitored by the probes of the detection instruments are constantly changing with time (such as heart and blood flow). In general, doctors operate probes in two states: a state where the probes are quickly moved to find a suspicious region; and a basically stationary or slight sliding state, focusing on the change of ultrasound images (such as a blood flow change) in a certain region with time. In the latter state, doctors usually use the medical image aided diagnosis system to draw an ROI on a dynamic image presented by a host computer display. The medical image aided diagnosis system will determine a time sequence of dynamic images corresponding to the ROI through the following steps. The specific descriptions are as follows:

In step 1, each frame in the dynamic image is pre-processed to output an image shown relatively fixed human organs regions such as bones, muscles, core heart regions (common part of contraction/diastole), or lung regions (common part of respiration), so as to obtain processed dynamic images in real time.

In step 2, a complete sequence of observation frames with relatively fixed probe positions in the dynamic image is obtained by the following two methods.

(1) Based on a position movement sensor, it is determined whether a probe is moving fast to look for an ROI, or is basically stationary (including slight moving) to observe the of the images which are change (such as blood flow change) with time in a certain region. Moreover, the complete sequence of observation frames with relatively fixed probe positions is directly determined according to the probe positions changing with time.

(2) Based on predictive coding between adjacent frames and inter-frame correlation calculation algorithms in MPEG4 compression algorithms, the processed dynamic image (the output image in step 1) is analyzed in real time to determine whether the probe is moving fast and looking for an ROI, or is basically stationary (including slight moving) and has been focusing on the change (such as blood flow change) of an image in a certain region with time, and a complete sequence of observation frames of the same scene is determined based on the analysis of adjacent frames and similar scenes (such algorithms have long been mature in MPEG4).

The MPEG4 compression algorithm provided in the second embodiment is provided with an algorithm module to detect whether the scene has changed ((including the detection of the telescopic transformation of a scene, that is, the detail enlarging of the same scene or scene expansion), scene translation, thorough scene switching). Medical dynamic images are generally mainly scene translation. There is less thorough, scene switching, which generally occurs when the probe is placed on a human body and removed. The descriptions are omitted herein.

In step 3, a complete sequence of observation frames where the ROI is located is completely acquired based on the foregoing ROI and the focus type determined by the expert, as well as a sequence of observation frames where it is located when the expert determines the ROI.

A frame sequence where the ROI is located when the expert determines the ROI refers to corresponding specific one or more continuous two-dimensional images (frames) when the expert determines the ROI. The system expands the two-dimensional image or part of two-dimensional dynamic image sequences corresponding to the ROI forward and backward to a complete sequence of observation frames (an entire period of time at which the probe position is relatively fixed). At this moment, the ROI of each extended frame may be simply processed and still limited to surround the two-dimensional ROI, and may also be further processed for image analysis based on the originally determined two-dimensional ROI and the focus type finally determined by the expert. A more accurate focus part is re-obtained in the extended frame through division.

Second, a focus type is determined according to the ROI and the candidate focus options, a lesion region is obtained through division according to the focus type, a structured report related to the ROI of the medical image of the patient is generated, and the lesion region and corresponding image semantic representation are added into a corresponding focus image library. When the candidate focus options do not match the ROI, the expert needs to manually input and send the image semantic representation corresponding to the ROI to other experts for verification, and after the verification is passed, the lesion region and the corresponding image semantic representation are added to the corresponding focus image library.

The situation that the candidate focus options do not match the ROI includes that the candidate focus options do not contain focus options corresponding to the ROI or the description of the ROI in the focus options is not accurate. The specific descriptions are as follows:

There is a possibility in the generated report that the pushed focus type is missing, that is, the expert believes that all candidate focus options recorded in the report cannot accurately describe the lesion region, and needs to manually input corresponding (known) focus names and corresponding attributes to be inserted into the report. This possibility exists especially when the system is not yet complete.

At this moment, the attribute of the focus and the corresponding local image of the focus will be recorded and added into the focus image library, and submitted to other experts for cross-validation as a new discovery that is inconsistent with the system judgment Once the new discovery is artificially confirmed, the corresponding knowledge (including the lesion region and the corresponding image semantic representation) will be added into the focus image library and added to a training set as a new training sample. When the system is updated regularly or irregularly, the new knowledge is added to the image semantic representation knowledge graph. If it is falsified by another expert, the manual entry result of this expert is corrected, and the recognition result of the system is adopted.

There is also a possibility in the generated report that the candidate focus options recorded in the report are missing, and it is necessary to input corresponding (unknown) focus names and corresponding attributes to be inserted into the report. This possibility may occur when the medical image aided diagnosis system is not yet complete, or may occur when a new type of focus is discovered.

At this moment, the new type of focus, along with the attributes and the corresponding focus local image, will be recorded and added into a temporary focus image library of the new type of focus, and submitted to other experts for cross-validation as a new discovered focus. Once the new discovery is artificially confirmed, the corresponding knowledge will be added into the image semantic representation knowledge graph, and the focus image will be added to the corresponding focus image library and added to a training set as a new training sample. If it is falsified by another expert, the manual entry result of this expert is corrected, and the previous recognition result of the medical image aided diagnosis system is adopted.

Generally speaking, the medical image aided diagnosis system may wait for such new samples to accumulate to a certain extent before training. When such samples are found, the medical image aided diagnosis system may also generate more similar samples based on the research and other knowledge of such new samples by experts in combination with a generative adversarial network (GAN), and perform learning when there are few samples.

Third Embodiment

The third embodiment provided by the invention provides a medical image aided diagnosis system combining image recognition and report editing. The system includes a knowledge graph establishment module, an information acquisition module, an ROI determination module, a candidate focus option generation module, a lesion region determination module, a report generation module, and a correction module. The knowledge graph establishment module is configured to establish an image semantic representation knowledge graph according to a standardized dictionary library in the field of images and historically accumulated medical image report analysis. The information acquisition module is configured to acquire a medical image of a patient. The ROI determination module is configured to determine an ROI of the medical image of the patient by an expert according to the medical image of the patient transmitted from the information acquisition module. The candidate focus option generation module is configured to provide candidate focus options of the patient according to the image semantic representation knowledge graph transmitted from the knowledge graph establishment module and the ROI transmitted from the ROI determination module. The lesion region determination module is configured to determine a focus type according to the ROI transmitted from the ROI determination module and the candidate focus options transmitted from the candidate focus option generation module, and perform division to obtain a lesion region according to the focus type. The report generation module is configured to generate a structured report related to the ROI of the medical image of the patient according to the divided lesion region and corresponding image semantic representation. The correction module is configured to add the lesion region and the corresponding image semantic representation into a corresponding focus image library.

The lesion region determination module includes a focus type determination unit and a lesion region determination unit. The focus type determination unit is configured to determine a focus type in the candidate focus options provided by the candidate focus option generation module according to the ROI transmitted from the ROI determination module. The lesion region determination unit is configured to perform localization analysis on the ROI transmitted from the ROI determination module, perform division to obtain a lesion region, and determine focus options corresponding to the lesion region according to the image semantic representation knowledge graph transmitted from the knowledge graph establishment module, so as to determine a lesion type.

In conclusion, according to the medical image aided diagnosis method combining image recognition and report editing provided by the invention, an image semantic representation knowledge graph and a variety of machine learning are combined to perform medical image recognition, sample images can be systematically and deeply accumulated, and the image semantic representation knowledge graph can be continuously improved, so that labeled focuses of many images can be continuously collected under the same sub-label. On the other hand, as more and more sample images of focuses with the same label are accumulated, the number of samples available for deep learning continues to increaser. The increase of samples generally leads to the enhancement of recognition capabilities and the improvement of recognition sensitivity and specificity. In addition, as more and more labeled focuses are accumulated, labeling of the focuses can be continuously refined by means of machine learning in combination with manual in-depth research, thereby further enriching the measures of radiomics, continuously refining image performance types of focuses, and enhancing aided diagnosis capabilities of medical images.

The medical image aided diagnosis method and system combining image recognition and report editing provided by the invention are described in detail above. Any obvious modification made by those of ordinary skill in the art to the present invention without departing from the essential of the present invention will constitute an infringement of the patent right of the present invention, and those of ordinary skill who make such modification shall bear corresponding legal liabilities.

What is claimed is:

1. A medical image aided diagnosis method combining image recognition and report editing, comprising the following steps:
   S1, establishing an image semantic representation knowledge graph of medical images;
   S2, obtaining a medical image of a patient, determining a region of interest (ROI) on a two-dimensional image, and providing candidate focus options of the patient according to the image semantic representation knowledge graph and the ROI; and
   S3, determining a focus type according to the ROI and the candidate focus options, dividing the medical image to obtain a lesion region according to the focus type, generating a structured report related to the ROI of the medical image of the patient, and adding the lesion region and corresponding image semantic representation into a corresponding focus image library;
   wherein step S3 further comprises the following steps:
   S301, performing localization analysis on the ROI based on the focus type to which the ROI belongs, calculating a spatial position of the ROI, to obtain the lesion region by dividing the medical image.

2. The medical image aided diagnosis method according to claim 1, wherein step S3 further comprises the following steps:
   S311, performing localization analysis on the ROI determined based on the focus type to which the ROI belongs, determining the focus type to which the ROI belongs, extending the determined ROI from a two-dimensional image to a three-dimensional stereoscopic image or a two-dimensional dynamic image, and dividing the lesion region from the medical image.

3. The medical image aided diagnosis method according to claim 2, wherein when an image type is a two-dimensional dynamic image, step S311 further comprises the following steps:
   step 1: calling a gray value of the two-dimensional image based on the focus type determined by an expert in combination with shape and texture features corresponding to the focus type, dividing the lesion region according to a connection relationship of organs, and obtaining a main closed region of a closed core focus region corresponding to the lesion region in a two-dimensional image section;
   step 2: extending to previous and next images in a spatial sequence of the two-dimensional images based on the main closed region, and dividing the lesion region according to the connection relationship of the organs based on the shape and texture features corresponding to the focus type, to obtain a closed region that matches the description of the focus type;
   step 3: continuing the operation in step 2, performing a mathematical morphological closed operation in a three-dimensional space, removing other regions connected to the closed core focus region in the three-dimensional space until the closed core focus region no longer expands, and delineating a closed core focus region edge; and
   step 4: calculating maximum and minimum values of X, Y, and Z axes in pixel point coordinates of the closed core focus region edge, forming a three-dimensional cube region.

4. The medical image aided diagnosis method according to claim 2, wherein when an image type is the two-dimensional dynamic image, step S311 further comprises the following steps:
   step 1: pre-processing each frame in the dynamic image, and outputting an image of relatively fixed human organs region;
   step 2: obtaining a complete sequence of observation frames with relatively fixed probe positions in the dynamic image; and
   step 3: completely obtaining the complete sequence of observation frames corresponding to the ROI, based on the ROI, the focus type determined, and a sequence of observation frames in which the ROI is determined.

5. The medical image aided diagnosis method according, to claim 4, wherein if a scanning probe does not have a position movement sensor, obtaining a complete sequence of observation frames with relatively fixed probe positions in the dynamic image in step 2 comprises the following steps:
   determining, based on the position movement sensor, whether the probe is moving fast;
   if the probe is moving fast, considering that it is looking for the ROI, otherwise, considering that the probe is basically stationary and is focusing on an image of a certain region that is changing with time; and
   determining the sequence of observation frames with relatively fixed probe positions based on the image changing with time.

6. The medical image aided diagnosis method according to claim 4, wherein if a scanning probe does not have a position movement sensor, obtaining a complete sequence of observation frames with relatively fixed probe positions in the dynamic image in step 2 comprises the following steps:
   analyzing the dynamic image in real time to determine whether the probe is moving fast;
   if the probe is moving fast, considering that it is looking for the ROI, otherwise, considering that the probe is basically stationary and is focusing on an image of a certain region that is changing with time; and
   determining the complete sequence of observation frames for the same scene based on analyzing adjacent frames and similar scenes.

7. The medical image aided diagnosis method according to claim 1, wherein
the structured report contains a hyperlink of the lesion region and an image semantic representation corresponding to the lesion region, and
the lesion region in the image and the image semantic representation corresponding to the lesion region can be viewed simultaneously by clicking the hyperlink.

8. The medical image aided diagnosis method according to claim 1, wherein
when the candidate focus options do not match the ROI, the image semantic representation corresponding to the ROI is input and sent to other experts for verification,
after the verification is passed, the lesion region and the corresponding image semantic representation are added to the corresponding focus image library.

9. A medical image aided diagnosis system combining image recognition and report editing, comprising: a knowledge graph establishment module, an information acquisition module, an ROI determination module, a candidate focus option generation module, a lesion region determination module, a report generation module, and a correction module,
wherein the knowledge graph establishment module is configured to establish an image semantic representation knowledge graph according to a standardized dictionary library in the field of images and accumulated medical image report analysis;
the information acquisition module is configured to acquire a medical image of a patient;
the ROI determination module is configured to determine an ROI of the medical image of the patient;
the candidate focus option generation module is configured to provide candidate focus options of the patient according to the image semantic representation knowledge graph and the ROI;
the lesion region determination module is configured to determine a focus type according to the ROI and the candidate focus options, and perform division to obtain a lesion region according to the focus type;
the report generation module is configured to generate a structured report related to the ROI of the medical image of the patient, according to the lesion region divided and the corresponding image semantic representation; and
the correction module is configured to add the lesion region and the corresponding image semantic representation into a corresponding focus image library;
wherein the lesion region determination module comprises a focus type determination unit and a lesion region determination unit; wherein
the focus type determination unit is configured to determine the focus type in the candidate focus options according to the ROI;
the lesion region determination unit is configured to perform localization analysis on the ROI, perform division to obtain a lesion region, and determine the lesion type corresponding to the lesion region according to the image semantic representation knowledge graph; and
the lesion region determination module is configured to perform localization analysis on the ROI, calculate a spatial position of the ROI, and perform division to obtain the lesion region.

10. A medical image aided diagnosis method combining image recognition and report editing, comprising the following steps:
S1, establishing an image semantic representation knowledge graph of medical images;
S2, obtaining a medical image of a patient, determining a region of interest (ROI) on a two-dimensional image, and providing candidate focus options of the patient according to the image semantic representation knowledge graph and the ROI; and
S3, determining a focus type according to the ROI and the candidate focus options, dividing the medical image to obtain a lesion region according to the focus type, generating a structured report related to the ROI of the medical image of the patient, and adding the lesion region and corresponding image semantic representation into a corresponding focus image library;
wherein in step S1, establishing an image semantic representation knowledge graph of medical images further comprises the following steps:
S11, forming a basic list of named entities based on a standardized dictionary library in the field of medical images;
S12, forming a characteristic description text specification for the named entities by analyzing accumulated medical image reports in the focus image library; and
S13, transforming the characteristic description text specification obtained for the named entities into the image semantic representation based on expert knowledge and a local lesion image corresponding to the focus type, and establishing the image semantic representation knowledge graph by each of the named entities, and the medical image and the image semantic representation corresponding to the each of the named entity.

* * * * *